US00PP10384P

United States Patent [19]

Meier et al.

[11] Patent Number: Plant 10,384

[45] Date of Patent: May 5, 1998

[54] BA 78-258 KENTUCKY BLUEGRASS

[75] Inventors: Virgil D. Meier, Marysville, Ohio; Jay B. Burr, Salem, Oreg.

[73] Assignee: OMS Investments, Inc., Wilmington, Del.

[21] Appl. No.: 763,076

[22] Filed: Dec. 10, 1996

[51] Int. Cl.[6] ..... A01H 5/00

[52] U.S. Cl. ..... Plt./90.2

[58] Field of Search ..... Plt./90.2

[56] References Cited

U.S. PATENT DOCUMENTS

| | | | |
|---|---|---|---|
| P.P. 3,156 | 5/1972 | Fuchigami et al. | Plt./90.2 |
| P.P. 3,186 | 5/1972 | Barenbrug et al. | Plt./90.2 |
| P.P. 4,336 | 11/1978 | Mayer et al. | Plt./90.2 |
| P.P. 6,280 | 9/1988 | Meier et al. | Plt./90.2 |
| P.P. 6,537 | 1/1989 | Meier et al. | Plt./90.2 |
| P.P. 6,538 | 1/1989 | Meier et al. | Plt./90.2 |
| P.P. 6,585 | 2/1989 | Meier et al. | Plt./90.2 |
| P.P. 7,831 | 3/1992 | Meier et al. | Plt./90.2 |
| P.P. 8,490 | 12/1993 | Meier et al. | Plt./90.2 |
| P.P. 9,036 | 1/1995 | Meier et al. | Plt./90.2 |
| P.P. 9,209 | 7/1995 | Meier et al. | Plt./90.2 |
| P.P. 9,611 | 7/1996 | Meier | Plt./90.2 |
| P.P. 9,848 | 4/1997 | Meier et al. | Plt./90.2 |
| P.P. 9,977 | 7/1997 | Meier et al. | Plt./90.2 |

*Primary Examiner*—James R. Feyrer

*Attorney, Agent, or Firm*—Jones, Day, Reavis & Pogue

[57] ABSTRACT

A variety of Kentucky Bluegrass having a medium to high level of resistance to leaf spot and melting out, dollar spot rusts and brown patch; a dark green color throughout the growing season; the ability to form a medium to high quality turf under a variety of environmental conditions; a moderately wide leaf blade; a strong root system and a high level of seed yielding capacity.

2 Drawing Sheets

BACKGROUND OF THE INVENTION

1. Field of the Invention

The present invention relates to a new and distinct variety of *Poa pratensis* that has been designated Ba 78-258 Kentucky Bluegrass.

2. Description of Related Art

Kentucky Bluegrasses have been dislcosed in U.S. Plant Pat. No. 3,156, issued May 9, 1972, U.S. Plant Pat. No. 3,186, issued May 23, 1972; U.S. Plant Patent No. 4,336, issued Nov. 28, 1978; U.S. Plant No. 6,280, issued Sep. 6, 1988; U.S. Plant Pat. Nos. 6,537 and 6,538, issued on Jan. 17, 1989; U.S. Plant Pat. No. 6,585, issued Feb. 7, 1989; U.S. Plant No. 7,831, issued Mar. 17, 1992; U.S. Plant Pat. No. 8,490, issued Dec. 7, 1993; U.S. Plant. Pat. No. 9,036, issued Jan. 3, 1995; U.S. Plant Pat. No. 9,209, issued Jul. 18, 1995; U.S. Plant Pat. No. 9,611, issued Jul. 23, 1996; and pending U.S. Plant patent applications Ser. No. 08/532,995, filed Sep. 22, 1995, now U.S. Plant Pat. No. 9,848, issued Apr. 1, 1997; Ser. No. 08/604,763, filed Feb. 23, 1996, now U.S. Plant Pat. No. 9,977, issued Jul. 22, 1997; Ser. No. 08/680,167, filed Jul. 15, 1996 and Ser. No. 08/680,168, filed Jul. 15, 1996.

SUMMARY OF THE VARIETY

Ba 78-258 plant material was selected from the open pollinated progeny of Ba70-62 Kentucky Bluegrass, a bluegrass plant maintained at The Scott Company's Research Station in Marysville, Ohio. After testing and observing the Ba 78-258 Kentucky Bluegrass variety, it was determined to be a distinct variety, and it was asexually propagated by rhizomes, tillers and disseminules.

Seed of Ba 78-258 Kentucky Bluegrass was produced first at Marysville, Ohio and later at Gervais, Oreg. This seed was used to plant turf performance evaluation trials and later seed production fields. Asexual production of Ba 78-258 by propagules (tillers and rhizomes) and by disseminules (modified caryopses produced by apomixis) has consistently produced progeny plants indistinguishable from the mother plant. The apomixis level of Ba 78-258 is approximately 95% based upon examining seedling characteristics of approximately 100 to 150 seedlings from different crop years in a growth chamber.

Ba 78-258 has a number of highly desirable characteristics including a medium to high level of resistance to (a) Dreschslera spp. that causes leaf spot, melting and out and crown rot; (b) *Sclerotinia homoeocarpa* that causes dollar spot; (c) Puccinia spp. that causes several types of rust infections; and (d) *Rhizoctonia solani* that causes brown patch. Ba 78-258 is an overall goof turfgrass performer as evidence by medium to high scores for quality and color. Ba 78-258 has a high seed yield potential in the Bluegrass seed production region of the northwestern United States.

In comparison with a number of other Kentucky Bluegrass varieties, Ba 78-258 has an average size seed and rachilla; significantly more hairs on the palea than other grasses; and an above average seed count. The panicle is above average in length and width; average in whorl number, and has an above average branch count for both the lower and third whorls. Ba 78-258 has average size spikelets, floret number and glumes. The peduncle is above average in length and width, and culm length; average in node number and internode length; and below average for internode color. The flag leaf and flag ligule are significantly longer than several other grasses. The leaf is above average in width and thickness and has above average hair content on the dosal side of the ligule and the leaf sheath margin. The leaf has below average hair on the leaf's margin and dosal side. The vegetative leaf and the vegetative ligule are above average in length; but, leaf width and thickness are close to average in comparison to other gases. The hair content of the vegetative leaf is as follows: (a) significantly greater than most other grasses for the upper margin of the ligule; (b) above average for the sheath margins and the leaf dosal side; and (c) below average for the leaf margins, and ventral sides, collar margins, and the dosal side of the sheath.

DETAILED DESCRIPTION OF THE VARIETY

Figure 1:
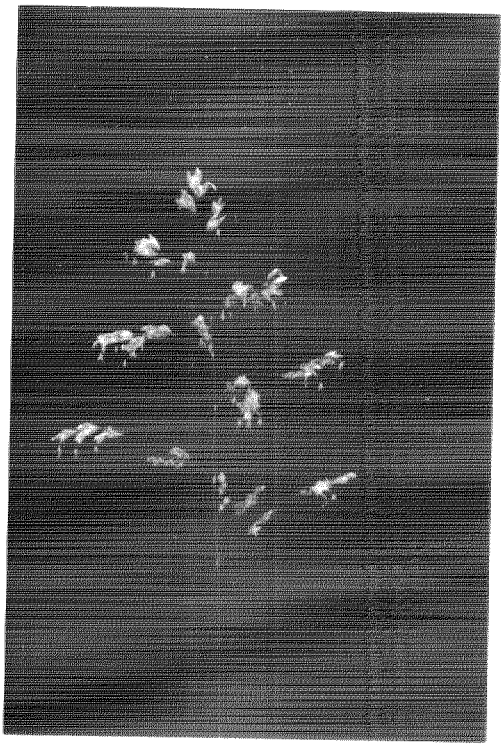
FIG. 1 is a Ba 78-258 Kentucky Bluegrass panicle.
Figure 2:
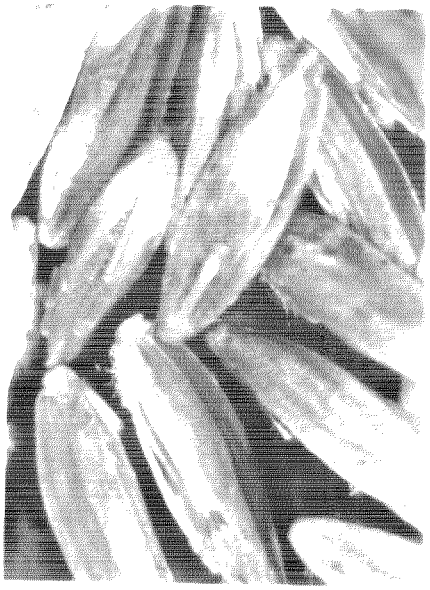
FIG. 2 is a Ba 78-258 Kentucky Bluegrass seed.
Figure 3:
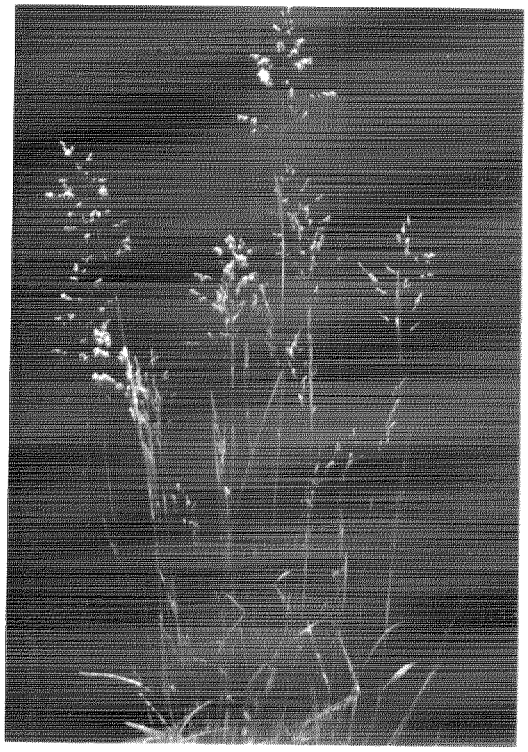
FIG. 3 is a Ba 78-258 Kentucky Bluegrass plant shortly after completing anthesis.

Ba 78-258 Kentucky Bluegrass (*Poa pratensis* L.) is perennial with creeping rhizomes forming a dense turf. When plants overwinter in the field under freezing temperatures and are then brought into the greenhouse during late winter to continue growth undistributed by clipping under moderate temperatures (60°–80° F.), culms are erect averaging 48.6 cm in length and 3.2 nodes per culm and the uppermost internode averages 13.6 cm in length. The peduncle averages 22.2 cm in length and 0.71 mm in width. The vegetative leaf averages 22.4 cm in length, 3.4 mm in width, 0.24 mm in thickness and a ligule length of 0.46 mm. The flag leaf averages 5.6 cm in length, 3.7 mm in width, 0.13 mm in thickness and a ligule length of 1.73 mm.

The panicle averages 90.3 mm in length, 56.6 mm in width, and 8.5 whorls. The lowest whorl and the third whorl from the bottom of the panicle average 2.8 and 3.5 branches, respectively. A spikelet in the lowest whorl averages 4.7 mm in length, 2.2 mm in width, 3.2 florets and the outer and inner glumes average 3.1 mm and 3.6 mm in length and 0.6 mm and 0.8 mm in width, respectively. A spikelet from the third whorl from the bottom of the panicle averages 4.5 mm in length, 2.3 mm in width, 3.3 florets and the outer and inner glumes average 3.0 mm and 3.5 mm in length and 0.5 mm and 0.7 mm in width, respectively.

The conditioned seed of Ba 78-258 averages 3.02 mm in length, 0.85 mm in width, and a rachilla length of 0.85 mm. The seed has a high level of hairs at the base of the lemma and palea margin.

Comparisons of Ba 78-258 with other Kentucky Bluegrass varieties in terms of seed dimensions and seed numbers per pound are shown in Table 1 and 2 as follows:

TABLE 1

Morphological Comparison of Seed Length and Width; Rachilla, and Lemma Hairs and Palea Hairs of Ba 78-258 and Other Kentucky Bluegrass Varieties After Conditioning.

| | Seed | | | Hairs* | |
|---|---|---|---|---|---|
| Variety | Length mm | Width mm | Rachilla mm | Lemma Base | Palea Margin |
| Ba 78-258 | 3.02 | 0.85 | 0.68 | 3.50 | 3.10 |
| Ba 78-165 | 3.32 | 0.97 | 0.50 | 4.00 | 1.60 |
| Ba 77-700 | 3.20 | 0.85 | 0.77 | 2.80 | 0.90 |
| Abbey | 3.02 | 0.85 | 0.56 | 1.80 | 0.40 |
| Ascot | 3.00 | 0.82 | 0.68 | 6.30 | 1.50 |
| Cannon | 3.32 | 0.85 | 0.72 | 0.20 | 2.00 |
| Gnome | 2.93 | 0.90 | 0.61 | 2.10 | 0.80 |
| Merit | 2.85 | 0.78 | 0.62 | 0.90 | 0.15 |
| Viva | 2.72 | 0.77 | 0.79 | 1.20 | 0.20 |
| LSD (.05) | 0.191 | 0.072 | 0.177 | 1.53 | 0.823 |

*Rating Scale: 0–9; 9 = most hairs

TABLE 2

Comparison of Seeds Per Pound of Ba 78-258 and Other Kentucky Bluegrass Varieties After Conditioning.

| Variety | Seeds Per Pound |
|---|---|
| Ba 78-258 | 1,127,000 |
| Ba 78-165 | 965,500 |
| Abbey | 988,500 |
| Buckingham | 978,000 |
| Cannon | 1,023,250 |
| Coventry | 1,374,750 |
| Garfield | 1,250,500 |
| Newport | 1,250,250 |
| Viva | 993,500 |
| LSD (.05) | 77,042 |

Ba 78-258 differs significantly from several of the Kentucky Bluegrass varieties in regard to the following morphological characteristics: (1) the culm and top internode length; (2) the flag leaf and flag leaf ligule; (3) significantly more hair for the upper margin of the vegetative leaf ligule; and (4) significantly more hairs on the palea. Since environmental conditions such as soil and climate may influence morphological characteristics to some extent, comparisons of morphological characteristics of Ba 78-258 were made with other Kentucky Bluegrass varieties and the comparisons are set forth in the following Tables 3–8:

TABLE 3

Morphological Comparison of Panicles, Whorl Number and Whorl Branches of Ba 78-258 and Other Kentucky Bluegrass Varieties in the Greenhouse at Marysville, OH.

| | Panicles | | | Number of Branches | |
|---|---|---|---|---|---|
| Variety | Length (mm) | Width (mm) | Whorl Number | Lowest Whorl | Third Whorl |
| Ba 78-258 | 90.3 | 56.6 | 8.5 | 3.8 | 3.5 |
| Ba 78-165 | 78.7 | 48.2 | 8.1 | 3.2 | 2.5 |
| Ba 77-700 | 87.7 | 57.9 | 8.2 | 3.9 | 3.3 |
| Abbey | 86.4 | 54.1 | 9.0 | 4.1 | 3.3 |
| Ascot | 91.4 | 60.7 | 9.1 | 2.4 | 2.3 |
| Cannon | 91.7 | 49.9 | 8.9 | 4.4 | 3.6 |
| Gnome | 85.4 | 43.7 | 9.1 | 3.6 | 3.4 |
| Merit | 77.3 | 38.9 | 8.1 | 2.9 | 2.8 |
| Viva | 82.5 | 46.6 | 8.0 | 3.4 | 3.0 |
| LSD (.05) | 8.03 | 8.83 | 0.65 | 0.71 | 0.59 |

TABLE 4

Morphological Comparison of Spikelets and Florets of Ba 78-258 and Other Kentucky Bluegrass Varieties in the Greenhouse at Marysville, OH.

| | Spikelets | | | | Number of Florets | |
|---|---|---|---|---|---|---|
| | Lowest Whorl | | Third Whorl | | Per Spikelet | |
| Variety | Length mm | Width mm | Length mm | Width mm | Lowest Whorl | Third Whorl |
| Ba 78-258 | 4.7 | 2.2 | 4.5 | 2.3 | 3.2 | 3.3 |
| Ba 78-165 | 4.3 | 2.1 | 4.5 | 2.2 | 2.8 | 2.9 |
| Ba 77-700 | 4.6 | 2.1 | 4.7 | 2.4 | 2.9 | 3.2 |
| Abbey | 5.0 | 2.3 | 4.9 | 2.3 | 3.3 | 3.3 |
| Ascot | 5.3 | 2.3 | 5.5 | 2.5 | 3.2 | 3.6 |
| Cannon | 4.7 | 2.0 | 4.8 | 2.1 | 3.2 | 3.1 |
| Gnome | 4.5 | 2.3 | 4.7 | 2.2 | 3.2 | 3.0 |

TABLE 4-continued

Morphological Comparison of Spikelets and Florets of Ba 78-258 and Other Kentucky Bluegrass Varieties in the Greenhouse at Marysville, OH.

| | Spikelets | | | | Number of Florets | |
|---|---|---|---|---|---|---|
| | Lowest Whorl | | Third Whorl | | Per Spikelet | |
| Variety | Length mm | Width mm | Length mm | Width mm | Lowest Whorl | Third Whorl |
| Merit | 5.0 | 2.5 | 5.2 | 2.5 | 3.9 | 3.8 |
| Viva | 4.9 | 1.9 | 5.0 | 2.0 | 3.3 | 3.3 |
| LSD (.05) | 0.43 | 0.35 | 0.46 | 0.34 | 0.52 | 0.59 |

TABLE 5

Morphological Comparison of Glumes of Ba 78-258 and Other Kentucky Bluegrass Varieties in the Greenhouse at Marysville, OH.

| | Outer Glume | | | |
|---|---|---|---|---|
| | Lowest Whorl | | Third Whorl | |
| Variety | Length mm | Width mm | Length mm | Width mm |
| Ba 78-258 | 3.1 | 0.6 | 3.0 | 0.5 |
| Ba 78-165 | 2.7 | 0.4 | 2.7 | 0.5 |
| Ba 77-700 | 3.0 | 0.6 | 2.9 | 0.6 |
| Abbey | 2.9 | 0.6 | 3.0 | 0.7 |
| Ascot | 3.9 | 0.6 | 4.0 | 0.7 |
| Cannon | 3.2 | 0.7 | 3.1 | 0.6 |
| Gnome | 2.8 | 0.6 | 2.9 | 0.6 |
| Merit | 3.0 | 0.6 | 3.0 | 0.6 |
| Viva | 3.1 | 0.5 | 3.1 | 0.5 |
| LSD (.05) | 0.29 | 0.12 | 0.29 | 0.13 |

| | Inner Glume | | | |
|---|---|---|---|---|
| | Lowest Whorl | | Third Whorl | |
| Variety | Length mm | Width mm | Length mm | Width mm |
| Ba 78-258 | 3.6 | 0.8 | 3.5 | 0.7 |
| Ba 78-165 | 3.2 | 0.6 | 3.4 | 0.6 |
| Ba 77-700 | 3.4 | 0.7 | 3.5 | 0.7 |
| Abbey | 3.4 | 0.9 | 3.5 | 0.8 |
| Ascot | 4.3 | 0.7 | 4.5 | 0.9 |
| Cannon | 3.5 | 0.8 | 3.5 | 0.8 |
| Gnome | 3.3 | 0.8 | 3.3 | 0.8 |
| Merit | 3.4 | 0.8 | 3.5 | 0.9 |
| Viva | 3.6 | 0.7 | 3.6 | 0.7 |
| LSD (.05) | 0.29 | 0.13 | 0.28 | 0.14 |

TABLE 6

Morphological Comparison of Flag Leaves of Ba 78-258 and Other Kentucky Bluegrass Varieties in the Greenhouse at Marysville, OH.

| | Leaf | | | |
|---|---|---|---|---|
| Variety | Length cm | Width mm | Thickness mm | Ligule Length mm |
| Ba 78-258 | 5.6 | 3.7 | 0.13 | 1.73 |
| Ba 78-165 | 4.0 | 3.5 | 0.12 | 1.45 |
| Ba 77-700 | 4.1 | 3.0 | 0.08 | 1.35 |
| Abbey | 4.7 | 3.6 | 0.12 | 1.53 |
| ***Ascot | 4.4 | 2.9 | 0.11 | 1.52 |
| Cannon | 5.3 | 3.7 | 0.12 | 1.75 |
| Gnome | 4.6 | 3.2 | 0.10 | 1.40 |

TABLE 6-continued

Morphological Comparison of Flag Leaves of Ba 78-258 and Other Kentucky Bluegrass Varieties in the Greenhouse at Marysville, OH.

| | | | | |
|---|---|---|---|---|
| Merit | 4.2 | 2.3 | 0.08 | 0.98 |
| Viva | 3.4 | 2.5 | 0.11 | 1.45 |
| LSD (.05) | 1.14 | 0.61 | 0.02 | 0.24 |

| | Hairs | | | |
|---|---|---|---|---|
| Variety | Ligule Dosal | Leaf Margin | Leaf Sheath Margin | Leaf Sheath Dosal |
| Ba 78-258 | 2.1 | 1.4 | 1.2 | 0.0 |
| Ba 78-165 | 2.0 | 0.2 | 0.1 | 0.0 |
| Ba 77-700 | 1.3 | 1.8 | 0.8 | 0.0 |
| Abbey | 1.9 | 2.2 | 1.3 | 0.6 |
| ***Ascot | 0.8 | 1.9 | 0.5 | 1.2 |
| Cannon | 1.4 | 2.4 | 0.8 | 0.0 |
| Gnome | 1.8 | 1.3 | 1.0 | 0.4 |
| Merit | 1.0 | 1.8 | 0.9 | 1.4 |
| Viva | 2.5 | 1.5 | 0.4 | 0.0 |
| LSD (.05) | 0.83 | 0.72 | 0.79 | 0.62 |

*Rating Scale: 0–9; 0 = none; 9 =0 many

TABLE 7

Morphological Comparison of Peduncles, Culms, Nodes Numbers Per Culm, Internode Length, and Internode Color or Ba 78-258 and Other Kentucky Bluegrass Varieties in the Greenhouse at Marysville, OH.

| | Peduncle | | Culm | Nodes | Internode* | Inter- |
|---|---|---|---|---|---|---|
| Variety | Length cm | Width mm | Length cm | Per Culm | Length cm | node** Color |
| Ba 78-258 | 22.2 | 0.71 | 48.6 | 3.2 | 13.6 | 0.3 |
| Ba 78-165 | 22.4 | 0.73 | 47.5 | 3.1 | 14.8 | 1.9 |
| Ba 77-700 | 21.6 | 0.68 | 50.6 | 3.2 | 14.7 | 0.2 |
| Abbey | 21.5 | 0.77 | 40.6 | 2.6 | 10.7 | 0.1 |
| Ascot | 17.5 | 0.68 | 41.9 | 3.1 | 14.6 | 1.6 |
| Cannon | 20.0 | 0.74 | 48.3 | 3.6 | 13.4 | 0.0 |
| Gnome | 17.3 | 0.69 | 40.6 | 3.2 | 10.6 | 1.2 |
| Merit | 23.6 | 0.66 | 44.1 | 3.0 | 11.8 | 0.8 |
| Viva | 19.7 | 0.55 | 50.7 | 3.5 | 14.9 | 0.0 |
| LSD (.05) | 2.6 | 0.8 | 2.6 | 0.5 | 1.2 | 0.8 |

*Top Internode
**Rating Scale: 0–9; = darkest color

TABLE 8

Morphological Comparison of Vegetative Leaves of Ba 78-258 and Other Kentucky Bluegrass Varieties in the Greenhouse at Marysville, OH.

| | Leaf | | | |
|---|---|---|---|---|
| Variety | Length cm | Width mm | Thickness mm | Ligule Length mm |
| Ba 78-258 | 22.4 | 3.4 | 0.24 | 0.46 |
| Ba 78-165 | 24.2 | 3.9 | 0.23 | 0.35 |
| Ba 77-700 | 23.2 | 3.5 | 0.23 | 0.50 |
| Abbey | 19.3 | 3.5 | 0.21 | 0.45 |
| Ascot | 20.4 | 3.2 | 0.21 | 0.42 |
| Cannon | 24.6 | 3.6 | 0.40 | 0.46 |
| Gnome | 19.5 | 3.8 | 0.24 | 0.48 |
| Merit | 21.8 | 3.6 | 0.23 | 0.41 |
| Viva | 25.0 | 3.2 | 0.24 | 0.40 |
| LSD (.05) | 3.67 | 0.42 | 0.14 | 0.06 |

TABLE 8-continued

Morphological Comparison of Vegetative Leaves of Ba 78-258 and Other Kentucky Bluegrass Varieties in the Greenhouse at Marysville, OH.

| | Hair* | | | |
|---|---|---|---|---|
| Variety | Ligule upper Margin | Color Margin | Sheath Margin | Sheath Dosal |
| Ba 78-258 | 7.7 | 2.1 | 4.1 | 4.7 |
| Ba 78-165 | 4.5 | 2.0 | 3.3 | 3.9 |
| Ba 77-700 | 7.3 | 2.9 | 3.1 | 5.3 |
| Abbey | 3.9 | 2.9 | 2.1 | 3.3 |
| Ascot | 4.1 | 3.5 | 3.0 | 3.2 |
| Cannon | 6.2 | 2.9 | 3.2 | 3.7 |
| Gnome | 5.6 | 3.9 | 2.9 | 3.1 |
| Merit | 5.4 | 3.2 | 3.7 | 3.0 |
| Viva | 6.6 | 4.5 | 4.3 | 3.9 |
| LSD (.05) | 1.10 | 0.87 | 1.21 | 0.98 |

| | Leaf Hairs* | | |
|---|---|---|---|
| Variety | Margin | Ventral | Dosal |
| Ba 78-258 | 0.6 | 0.4 | 1.0 |
| Ba 78-165 | 1.3 | 0.2 | 1.7 |
| Ba 77-700 | 1.5 | 0.2 | 0.1 |
| Abbey | 0.4 | 1.0 | 0.2 |
| Ascot | 0.9 | 0.0 | 0.9 |
| Cannon | 0.4 | 0.9 | 0.7 |
| Gnome | 1.0 | 0.9 | 0.5 |
| Merit | 0.1 | 0.5 | 0.0 |
| Viva | 1.5 | 0.2 | 0.2 |
| LSD (.05) | 0.75 | 0.61 | 0.54 |

*Rating Scale: 0–9; 0 = none; 9 = many

Ba 78-258 has performed well throughout the U.S. as exhibited by medium to high turf quality ratings in comparison to many other Kentucky Bluegrass varieties. In addition, it has a dark green color which can be maintained throughout the growing season.

With regard to comparative analysis conducted for purposes of determining color of Ba 78-258 plants relative to other Kentucky Bluegrass varieties, readings were taken of the vegetative color of Ba 78-258 during mid-October while the turf was actively growing with adequate nutrient with water availability. The readings were taken in full sun with several actively growing leaves being compared, one at a time, utilizing color chips from the Munsell Book of Color as a reference. On this basis, the color of Ba 78-258 was determined to be 5 GY 4/6. During the same time period, the color of similar leaves of other Kentucky Bluegrass varieties were determined by the same procedure to be as follows: Ascot — 5 Gy 4/4; Buckingham — 7.5 GY 4/4; Ba77-700 — 5 GY 4/6; Midnight — 7.5 GY 4/4, Abbey — 5 GY 4/6; and Victa — 5 GY 4/4. However, it should be noted that the general apparent color of turf does not always correlate directly with the color of the individual actively growing leaves within the turf and that turf color varies with nutrient level and time of year with some varieties being darker or lighter green depending on such factors.

Comparisons of Ba 78-258 with other Kentucky Bluegrass varieties for quality, genetic color, winter color, leaf texture, drought tolerance including wilting, dormancy and recovery are set forth hereinafter in Tables 9–18:

TABLE 9

A Comparison of Quality of Ba 78-258 and Other Kentucky Bluegrass Varieties at Six (6) Locations in the U.S.

| | Test Locations | | | | | |
|---|---|---|---|---|---|---|
| Variety | Fort Collins | Post Falls | Lexington | Marysville | Beltsville | Blacksburg |
| Ba 78-258 | 8.7 | 6.1 | 6.1 | 6.8 | 6.7 | 4.9 |
| Ba 77-700 | 8.0 | 5.1 | 5.5 | 6.2 | 6.7 | 4.9 |
| Abbey | 7.0 | 5.1 | 6.2 | 6.7 | 6.8 | 5.0 |
| Able 1 | 7.7 | 7.3 | 5.4 | 7.0 | 6.5 | 5.0 |
| Allure | 8.7 | 6.2 | 5.8 | 7.3 | 7.1 | 4.6 |
| Ascot | 9.0 | 7.7 | 5.5 | 5.8 | 7.4 | 4.9 |
| A-34 | 8.7 | 5.9 | 5.2 | 7.0 | 6.2 | 4.9 |
| Banff | 8.7 | 6.2 | 6.6 | 6.8 | 6.7 | 5.1 |
| Baron | 7.7 | 5.4 | 6.4 | 7.0 | 7.0 | 5.7 |
| Buckingham | 7.3 | 7.3 | 4.4 | 5.5 | 6.3 | 4.1 |
| Cannon | 8.0 | 5.1 | 5.7 | 6.5 | 6.8 | 5.1 |
| Challenger | 8.7 | 7.3 | 5.2 | 6.7 | 6.6 | 4.1 |
| Classic | 8.3 | 5.5 | 5.6 | 6.8 | 6.7 | 4.8 |
| Coventry | 8.7 | 7.2 | 6.5 | 6.7 | 7.0 | 4.7 |
| Eclipse | 8.3 | 5.9 | 6.9 | 6.2 | 7.3 | 5.0 |
| Estate | 8.7 | 6.4 | 6.0 | 7.0 | 6.4 | 5.0 |
| Fairfax | 8.7 | 6.7 | 5.8 | 6.8 | 6.8 | 4.9 |
| Georgetown | 8.0 | 6.3 | 6.0 | 6.5 | 6.9 | 4.4 |
| Glade | 9.0 | 7.5 | 6.8 | 7.0 | 7.6 | 4.3 |
| Gnome | 8.0 | 5.2 | 5.8 | 7.0 | 7.0 | 5.0 |
| Haga | 8.0 | 5.9 | 6.4 | 7.0 | 6.8 | 4.5 |
| Kelly | 7.7 | 5.7 | 6.0 | 6.5 | 6.8 | 5.0 |
| Kenblue | 7.7 | 2.7 | 4.9 | 7.0 | 6.2 | 3.9 |
| Liberty | 8.3 | 6.5 | 5.5 | 6.5 | 6.7 | 4.7 |
| Merion | 6.7 | 2.7 | 3.8 | 5.2 | 4.8 | 3.2 |
| Merit | 8.0 | 4.8 | 5.9 | 6.5 | 6.6 | 5.0 |
| Midnight | 8.0 | 7.9 | 6.7 | 6.7 | 7.7 | 4.9 |
| Monopoly | 7.7 | 4.9 | 6.0 | 7.3 | 6.1 | 5.1 |
| Nassau | 8.0 | 5.8 | 6.0 | 6.0 | 6.3 | 4.8 |
| Ram 1 | 8.0 | 7.3 | 5.3 | 7.3 | 7.0 | 5.3 |
| So. Dakota | 7.0 | 4.3 | 4.7 | 6.2 | 4.9 | 3.0 |
| Touchdown | 9.0 | 7.1 | 5.3 | 6.7 | 6.5 | 4.7 |
| Viva | 7.7 | 5.1 | 5.5 | 6.5 | 6.6 | 4.9 |
| LSD (.05) | 1.2 | 1.1 | 1.0 | 1.1 | 0.5 | 0.9 |

Rating Scale: 1–9; 9 = Ideal Turf

TABLE 10

A Comparison of Quality of Ba 78-258 and Other Kentucky Bluegrass Varieties at Four (4) Locations in the U.S.

| | Test Locations | | | |
|---|---|---|---|---|
| Variety | Urbana IL | Marysville OH | Hubbard OR | Pullman WA |
| Ba 78-258 | 5.5 | 7.0 | 5.6 | 6.3 |
| Ba 77-700 | 4.8 | 6.7 | 4.6 | 5.8 |
| Abbey | 4.8 | 6.0 | 4.9 | 6.5 |
| Able 1 | 5.5 | 7.0 | 5.4 | 5.8 |
| Allure | 6.0 | 7.0 | 6.4 | 5.9 |
| Ascot | 4.9 | 7.0 | 6.7 | 6.5 |
| A-34 | 6.0 | 7.0 | 5.3 | 5.5 |
| Banff | 5.6 | 6.7 | 5.3 | 6.1 |
| Baron | 5.3 | 7.0 | 5.8 | 6.1 |
| Buckingham | 4.3 | 6.0 | 4.9 | 6.1 |
| Cannon | 5.1 | 6.3 | 4.7 | 5.7 |
| Challenger | 5.0 | 7.3 | 5.4 | 6.3 |
| Classic | 6.2 | 6.3 | 4.5 | 6.2 |
| Coventry | 6.0 | 7.0 | 5.9 | 6.1 |
| Eclipse | 5.9 | 7.0 | 5.3 | 6.1 |
| Estate | 5.9 | 7.3 | 6.6 | 6.2 |
| Fairfax | 6.5 | 6.3 | 6.5 | 6.1 |
| Georgetown | 5.2 | 6.7 | 4.9 | 6.3 |
| Glade | 5.8 | 7.0 | 5.0 | 6.3 |
| Gnome | 4.7 | 6.3 | 4.1 | 5.9 |
| Haga | 5.5 | 7.0 | 5.2 | 6.4 |
| Kelly | 5.0 | 6.7 | 4.4 | 5.5 |
| Kenblue | 4.8 | 4.0 | 4.3 | 5.2 |

TABLE 10-continued

A Comparison of Quality of Ba 78-258 and Other Kentucky Bluegrass Varieties at Four (4) Locations in the U.S.

| Variety | Urbana IL | Marysville OH | Hubbard OR | Pullman WA |
|---|---|---|---|---|
| | Test Locations | | | |
| Liberty | 5.3 | 6.7 | 5.6 | 6.3 |
| Merion | 3.8 | 6.7 | 4.1 | 6.2 |
| Merit | 4.8 | 6.3 | 4.3 | 6.0 |
| Midnight | 5.0 | 7.0 | 4.2 | 6.2 |
| Monopoly | 6.0 | 6.7 | 4.4 | 5.3 |
| Nassau | 4.2 | 6.7 | 4.9 | 6.3 |
| Ram 1 | 5.0 | 7.0 | 5.6 | 6.7 |
| So. Dakota | 4.2 | 3.7 | 2.7 | 5.3 |
| Touchdown | 5.6 | 6.3 | 3.3 | 6.4 |
| Viva | 4.8 | 6.0 | 4.9 | 6.2 |
| LSD (.05) | 0.9 | 0.9 | 1.1 | 0.7 |

Rating Scale: 1–9; 9 = Ideal Turf

TABLE 11

A Comparison of Quality of Ba 78-258 and Other Kentucky Bluegrass Varieties at Five (5) Locations in the U.S.

| Variety | Fort Collins CO | Urbana IL | Martinsville NJ | Kingston RI | Pullman WA |
|---|---|---|---|---|---|
| | Test Locations | | | | |
| Ba 78-258 | 6.7 | 4.6 | 5.4 | 5.7 | 5.9 |
| Ba 77-700 | 6.3 | 3.9 | 4.4 | 5.7 | 5.3 |
| Abbey | 6.3 | 3.6 | 4.7 | 5.7 | 5.6 |
| Able 1 | 6.3 | 4.2 | 6.1 | 5.8 | 5.6 |
| Allure | 5.9 | 5.5 | 5.4 | 5.3 | 5.8 |
| Ascot | 6.7 | 4.2 | 6.0 | 5.7 | 6.0 |
| A-34 | 5.2 | 4.6 | 5.0 | 5.6 | 5.2 |
| Banff | 6.1 | 4.0 | 5.0 | 5.0 | 5.4 |
| Baron | 5.3 | 4.1 | 5.0 | 5.7 | 5.8 |
| Buckingham | 5.6 | 2.9 | 5.4 | 4.6 | 5.7 |
| Cannon | 6.1 | 4.0 | 4.3 | 5.4 | 6.0 |
| Challenger | 6.1 | 3.2 | 5.3 | 5.2 | 5.3 |
| Classic | 5.8 | 4.8 | 4.9 | 5.4 | 5.9 |
| Coventry | 6.1 | 5.4 | 5.0 | 5.0 | 5.9 |
| Eclipse | 6.6 | 5.0 | 5.9 | 6.1 | 6.3 |
| Estate | 5.8 | 4.7 | 5.1 | 5.2 | 5.6 |
| Fairfax | 5.9 | 5.3 | 4.8 | 5.3 | 5.7 |
| Georgetown | 5.8 | 4.3 | 5.0 | 5.3 | 5.4 |
| Glade | 6.1 | 5.2 | 4.6 | 5.8 | 4.9 |
| Gnome | 5.9 | 3.6 | 4.7 | 5.4 | 5.7 |
| Haga | 5.6 | 4.2 | 4.8 | 5.2 | 5.4 |
| Kelly | 5.9 | 4.3 | 4.2 | 5.2 | 5.3 |
| Kenblue | 3.7 | 4.2 | 2.8 | 4.9 | 3.9 |
| Liberty | 6.2 | 4.5 | 5.2 | 5.3 | 6.0 |
| Merion | 5.1 | 3.1 | 4.1 | 5.4 | 5.8 |
| Merit | 6.1 | 4.6 | 5.1 | 5.7 | 5.9 |
| Midnight | 7.1 | 4.3 | 7.3 | 5.1 | 6.1 |
| Monopoly | 4.7 | 5.7 | 4.6 | 5.5 | 5.3 |
| Nassau | 5.8 | 3.0 | 5.2 | 5.2 | 5.6 |
| Ram 1 | 6.1 | 3.8 | 4.7 | 5.7 | 4.7 |
| So. Dakota | 4.1 | 3.6 | 2.1 | 4.6 | 3.7 |
| Touchdown | 6.4 | 4.5 | 5.3 | 5.2 | 6.0 |
| Viva | 6.1 | 4.0 | 4.4 | 5.9 | 5.8 |
| LSD (.05) | 0.7 | 1.1 | 0.9 | 0.7 | 0.7 |

Rating Scale: 1–9; 9 = Ideal Turf

TABLE 12

A Comparison of Quality of Ba 78-258 and Other Kentucky Bluegrass Varieties at Four (4) Locations in the U.S.

| Variety | Ames IA | Hubbard OR | Kingston RI | Haymarket VA |
|---|---|---|---|---|
| | Test Locations | | | |
| Ba 78-258 | 7.3 | 4.9 | 5.8 | 5.3 |
| Ba 77-700 | 6.9 | 3.7 | 6.0 | 5.4 |
| Abbey | 6.8 | 3.2 | 5.7 | 5.4 |
| Able 1 | 7.2 | 5.4 | 5.9 | 3.6 |
| Allure | 7.4 | 5.6 | 5.0 | 5.7 |
| Ascot | 7.8 | 6.1 | 5.8 | 4.2 |
| A-34 | 7.2 | 4.0 | 5.4 | 4.7 |
| Banff | 7.0 | 3.7 | 4.6 | 4.4 |
| Baron | 6.9 | 3.7 | 5.6 | 5.7 |
| Buckingham | 6.7 | 3.8 | 4.4 | 4.4 |
| Cannon | 6.7 | 3.8 | 5.2 | 5.4 |
| Challenger | 7.1 | 3.8 | 4.7 | 5.2 |
| Classic | 7.1 | 3.6 | 4.9 | 4.8 |
| Coventry | 7.3 | 5.1 | 5.3 | 5.8 |
| Eclipse | 7.1 | 3.2 | 6.0 | 4.9 |
| Estate | 7.7 | 5.2 | 5.5 | 5.7 |
| Fairfax | 7.4 | 5.1 | 5.6 | 5.7 |
| Georgetown | 7.2 | 3.1 | 5.4 | 4.9 |
| Glade | 7.1 | 2.9 | 4.8 | 5.8 |
| Gnome | 7.1 | 3.0 | 5.5 | 5.7 |
| Haga | 7.0 | 3.4 | 5.1 | 5.1 |
| Kelly | 6.9 | 4.0 | 5.3 | 5.5 |
| Kenblue | 5.8 | 2.9 | 4.5 | 4.7 |
| Liberty | 7.1 | 3.6 | 5.3 | 4.2 |
| Merion | 6.9 | 3.7 | 5.4 | 5.6 |
| Merit | 6.9 | 3.9 | 5.7 | 5.3 |
| Midnight | 8.2 | 3.2 | 5.0 | 5.2 |
| Monopoly | 6.9 | 3.1 | 5.2 | 4.8 |
| Nassau | 6.9 | 4.0 | 4.9 | 5.2 |
| Ram 1 | 7.2 | 3.3 | 5.2 | 5.2 |
| So. Dakota | 6.1 | 2.8 | 4.8 | 4.8 |
| Touchdown | 7.0 | 3.0 | 4.5 | 4.3 |
| Viva | 6.9 | 3.4 | 5.6 | 5.8 |
| LSD (.05) | 0.5 | 1.4 | 0.8 | 1.0 |

Rating Scale: 1–9; 9 = Ideal Turf

TABLE 13

A Comparison of Genetic Color of Ba 78-258 and Other Kentucky Bluegrass Varieties in Four (4) Tests A–D Conducted at Various Locations in the U.S.

| Variety | A | B | C | D |
|---|---|---|---|---|
| | Tests (Mean Values) | | | |
| Ba 78-258 | 5.9 | 5.7 | 5.8 | 6.4 |
| Ba 77-700 | 5.7 | 5.5 | 5.8 | 6.3 |
| Abbey | 5.6 | 5.9 | 5.8 | 6.7 |
| Able 1 | 6.6 | 6.8 | 6.8 | 6.9 |
| Allure | 5.7 | 5.2 | 5.6 | 5.7 |
| Ascot | 6.9 | 6.8 | 7.2 | 7.4 |
| A-34 | 5.0 | 5.4 | 4.6 | 5.7 |
| Banff | 5.1 | 6.0 | 5.5 | 5.8 |
| Baron | 6.0 | 6.0 | 5.9 | 6.6 |
| Buckingham | 7.0 | 7.2 | 7.2 | 7.2 |
| Cannon | 6.0 | 5.7 | 6.4 | 6.6 |
| Challenger | 6.0 | 6.2 | 5.9 | 5.9 |
| Classic | 5.2 | 5.9 | 5.2 | 5.9 |
| Coventry | 5.9 | 5.6 | 5.8 | 6.0 |
| Eclipse | 6.3 | 6.6 | 6.4 | 7.2 |
| Estate | 5.8 | 5.3 | 5.3 | 6.3 |
| Fairfax | 6.0 | 5.4 | 5.4 | 5.9 |
| Georgetown | 5.2 | 6.1 | 5.3 | 6.2 |
| Glade | 6.7 | 6.3 | 6.7 | 6.6 |
| Gnome | 6.0 | 6.1 | 5.8 | 6.7 |
| Haga | 5.1 | 5.8 | 5.3 | 6.1 |
| Kelly | 5.6 | 5.7 | 6.1 | 6.8 |

TABLE 13-continued

A Comparison of Genetic Color of Ba 78-258 and Other Kentucky Bluegrass Varieties in Four (4) Tests A–D Conducted at Various Locations in the U.S.

| | Tests (Mean Values) | | | |
|---|---|---|---|---|
| Variety | A | B | C | D |
| Kenblue | 4.6 | 5.0 | 5.3 | 5.6 |
| Liberty | 5.9 | 6.1 | 6.1 | 6.4 |
| Merion | 5.7 | 5.8 | 5.4 | 6.0 |
| Merit | 5.7 | 5.7 | 6.2 | 6.6 |
| Midnight | 7.1 | 7.3 | 7.7 | 7.6 |
| Monopoly | 4.8 | 4.9 | 4.8 | 4.7 |
| Nassau | 6.0 | 6.6 | 6.5 | 6.8 |
| Ram 1 | 6.7 | 5.9 | 6.6 | 6.2 |
| So. Dakota | 4.5 | 4.8 | 4.7 | 5.8 |
| Touchdown | 5.5 | 5.5 | 5.3 | 6.1 |
| Viva | 5.5 | 5.5 | 5.9 | 6.6 |
| LSD (.05) | 0.5 | 0.4 | 0.7 | 0.8 |

Genetic Color Rating Scale: 1–9; 9 = Dark Green

TABLE 14

A Comparison of Winter Color of Ba 78-258 and Other Kentucky Bluegrass Varieties in Two (2) Tests A–B Conducted at Various Locations in the U.S.

| Variety | Test A* | Test B** |
|---|---|---|
| Ba 78-258 | 6.0 | 4.7 |
| Ba 77-700 | 5.0 | 5.0 |
| Abbey | 1.7 | 6.3 |
| Able 1 | 6.3 | 3.3 |
| Allure | 6.0 | 6.3 |
| Ascot | 4.7 | 4.3 |
| A-34 | 6.7 | 2.0 |
| Banff | 9.0 | 3.7 |
| Baron | 2.3 | 5.7 |
| Buckingham | 5.3 | 6.3 |
| Cannon | 2.3 | 6.0 |
| Challenger | 7.3 | 4.3 |
| Classic | 9.0 | 3.3 |
| Coventry | 7.0 | 3.7 |
| Eclipse | 4.7 | 3.7 |
| Estate | 5.7 | 5.0 |
| Fairfax | 6.0 | 4.5 |
| Georgetown | 8.0 | 3.3 |
| Glade | 1.7 | 3.7 |
| Gnome | 1.0 | 5.7 |
| Haga | 9.0 | 3.0 |
| Kelly | 2.3 | 5.7 |
| Kenblue | 1.3 | 3.0 |
| Liberty | 7.3 | 3.3 |
| Merion | 6.7 | 3.3 |
| Merit | 3.7 | 6.0 |
| Midnight | 3.0 | 1.7 |
| Monopoly | 4.3 | 2.7 |
| Nassau | 7.7 | 5.0 |
| Ram 1 | 1.7 | 3.7 |
| So. Dakota | 2.3 | 4.0 |
| Touchdown | 3.0 | 2.3 |
| Viva | 2.3 | 4.0 |
| LSD (.05) | 1.9 | 2.1 |

Winter Color Rating Scale; 1–9; 9 = Complete Color Retention
*Location: North Brunswick, NJ
**Location: Post Falls, ID

TABLE 15

A Comparison of Leaf Texture of Ba 78-258 and Other Kentucky Bluegrass Varieties in Two (2) Test A–B Conducted at Various Locations in the U.S.

| Variety | Test A* | Test B* |
|---|---|---|
| Ba 78-258 | 4.7 | 4.0 |
| Ba 77-700 | 4.0 | 4.0 |
| Abbey | 5.0 | 4.3 |
| Able 1 | 5.7 | 6.3 |
| Allure | 4.3 | 4.0 |
| Ascot | 5.3 | 6.0 |
| A-34 | 4.3 | 5.2 |
| Banff | 5.3 | 5.2 |
| Baron | 5.0 | 4.2 |
| Buckingham | 4.0 | 3.7 |
| Cannon | 4.0 | 4.0 |
| Challenger | 5.0 | 4.5 |
| Classic | 5.3 | 5.3 |
| Coventry | 5.0 | 4.2 |
| Eclipse | 5.7 | 5.7 |
| Estate | 4.3 | 3.8 |
| Fairfax | 4.7 | 4.0 |
| Georgetown | 6.0 | 4.8 |
| Glade | 5.0 | 4.8 |
| Gnome | 5.3 | 4.2 |
| Haga | 5.7 | 5.2 |
| Kelly | 4.3 | 4.0 |
| Kenblue | 6.0 | 5.8 |
| Liberty | 5.0 | 4.7 |
| Merion | 4.0 | 4.2 |
| Merit | 4.7 | 4.0 |
| Midnight | 6.7 | 6.0 |
| Monopoly | 5.0 | 4.5 |
| Nassau | 5.0 | 4.3 |
| Ram 1 | 5.0 | 4.8 |
| So. Dakota | 3.7 | 4.8 |
| Touchdown | 5.3 | 5.8 |
| Viva | 4.3 | 4.0 |
| LSD (.05) | 0.9 | 0.8 |

Leaf Texture Rating Scale: 1–9; 9 = very fine
*Locations: Martinsville, NJ; pooled data from Halsey, Hubbard, and Gervais, OR.

TABLE 16

A Comparison of Drought Tolerance (Wilting) of Ba 78-258 and Other Kentucky Varieties in a Test A Conducted at Richmond Hills, Canada.

| Variety | Test A |
|---|---|
| Ba 78-258 | 5.3 |
| Ba 77-700 | 5.0 |
| Abbey | 5.0 |
| Able 1 | 5.3 |
| Allure | 4.3 |
| Ascot | 4.0 |
| A-34 | 5.3 |
| Banff | 4.7 |
| Baron | 4.7 |
| Buckingham | 4.3 |
| Cannon | 5.0 |
| Challenger | 4.7 |
| Classic | 4.7 |
| Coventry | 4.7 |
| Eclipse | 5.0 |
| Estate | 5.3 |
| Fairfax | 4.3 |
| Georgetown | 4.7 |
| Glade | 5.0 |
| Gnome | 4.0 |
| Haga | 4.3 |
| Kelly | 5.0 |
| Kenblue | 4.3 |
| Liberty | 5.0 |
| Merion | 5.0 |

TABLE 16-continued

A Comparison of Drought Tolerance (Wilting) of Ba 78-258 and Other Kentucky Varieties in a Test A Conducted at Richmond Hills, Canada.

| Variety | Test A |
|---|---|
| Merit | 4.3 |
| Midnight | 4.7 |
| Monopoly | 5.0 |
| Nassau | 4.0 |
| Ram 1 | 4.7 |
| So. Dakota | 4.3 |
| Touchdown | 4.7 |
| Viva | 5.0 |
| LSD (.05) | 1.2 |

Drought Tolerance (Wilting) Rating Scale: 1–9; 9 = No Wilting

TABLE 17

A Comparison of Drought Tolerance (Dormancy) of Ba 78-258 and Other Kentucky Bluegrass Varieties in a Test A Conducted at Haymarket, VA.

| Variety | Test A |
|---|---|
| Ba 78-258 | 4.7 |
| Ba 77-700 | 5.3 |
| Abbey | 4.3 |
| Able 1 | 3.3 |
| Allure | 4.0 |
| Ascot | 4.0 |
| A-34 | 3.0 |
| Banff | 3.3 |
| Baron | 4.0 |
| Buckingham | 4.0 |
| Cannon | 4.0 |
| Challenger | 3.3 |
| Classic | 3.7 |
| Coventry | 3.7 |
| Eclipse | 4.3 |
| Estate | 4.3 |
| Fairfax | 4.3 |
| Georgetown | 3.7 |
| Glade | 5.0 |
| Gnome | 3.7 |
| Haga | 3.0 |
| Kelly | 4.0 |
| Kenblue | 4.0 |
| Liberty | 3.0 |
| Merion | 3.7 |
| Merit | 4.7 |
| Midnight | 3.7 |
| Monopoly | 4.0 |
| Nassau | 3.3 |
| Ram 1 | 4.3 |
| So. Dakota | 4.0 |
| Touchdown | 4.0 |
| Viva | 4.7 |
| LSD (.05) | 1.1 |

Drought Tolerance (Dormancy) Rating Scale: 1–9; 9 = No Dormancy

TABLE 18

A Comparison of Drought Tolerance (Recovery) of Ba 78-258 and Other Kentucky Bluegrass Varieties in a Test A Conducted at Various Locations in the U.S.

| Variety | Test A* (Mean Values) |
|---|---|
| Ba 78-258 | 5.3 |
| Ba 77-700 | 4.8 |
| Abbey | 4.5 |
| Able 1 | 4.3 |
| Allure | 4.7 |
| Ascot | 3.2 |

TABLE 18-continued

A Comparison of Drought Tolerance (Recovery) of Ba 78-258 and Other Kentucky Bluegrass Varieties in a Test A Conducted at Various Locations in the U.S.

| Variety | Test A* (Mean Values) |
|---|---|
| A-34 | 3.3 |
| Banff | 3.5 |
| Baron | 5.5 |
| Buckingham | 2.8 |
| Cannon | 4.3 |
| Challenger | 3.5 |
| Classic | 4.2 |
| Coventry | 4.7 |
| Eclipse | 3.3 |
| Estate | 5.5 |
| Fairfax | 5.0 |
| Georgetown | 3.5 |
| Glade | 4.2 |
| Gnome | 4.8 |
| Haga | 4.0 |
| Kelly | 4.5 |
| Kenblue | 4.8 |
| Liberty | 4.2 |
| Merion | 3.5 |
| Merit | 5.7 |
| Midnight | 4.5 |
| Monopoly | 4.7 |
| Nassau | 5.0 |
| Ram 1 | 4.3 |
| So. Dakota | 3.7 |
| Touchdown | 4.3 |
| Viva | 4.8 |
| LSD (.05) | 1.2 |

Drought Recovery Rating Scale: 1–9; 9 = Complete Recovery
*Locations: Carbondale, IL; pooled data from Halsey, Hubbard and Gervais, OR.

Turf diseases are one of the major causes of inconsistent and poor turf performance. Ba 78-258 has been found to have a medium to high level of resistance to the following diseases: (a) leaf spot and melting out caused by *Dreschslera poae* formerly called *Helminthosporium vagans*; (b) dollar spot caused by *Sclerotinia homoecarpa*; (c) several diseases of rusts caused by Puccinia spp.; and (d) brown patch caused by *Rhizoctonia solani*.

Comparisons of disease incidence of Ba 78-258 as compared with other Kentucky Bluegrass varieties in regard to leaf spot, dollar spot, rusts, and brown patch are presented in Tables 19–24.

TABLE 19

A Comparison of Leaf Spot incidence IN Ba 78-258 and Other Kentucky Bluegrass Varieties in Two (2) Tests Conducted at Various Locations in the U.S.

| | Means | |
|---|---|---|
| Variety | Test 1* | Test 2** |
| Ba 78-258 | 5.8 | 6.9 |
| Ba 77-700 | 5.7 | 7.2 |
| Abbey | 5.1 | 7.8 |
| Able 1 | 7.1 | 7.8 |
| Allure | 5.8 | 7.7 |
| Ascot | 7.4 | 8.1 |
| A-34 | 5.4 | 7.2 |
| Banff | 5.9 | 7.8 |
| Baron | 5.4 | 7.1 |
| Buckingham | 6.8 | 8.3 |
| Cannon | 5.8 | 8.0 |
| Challenger | 6.9 | 8.0 |

TABLE 19-continued

A Comparison of Leaf Spot incidence IN Ba 78-258 and Other Kentucky Bluegrass Varieties in Two (2) Tests Conducted at Various Locations in the U.S.

| | Means | |
|---|---|---|
| Variety | Test 1* | Test 2** |
| Classic | 5.4 | 7.8 |
| Coventry | 5.8 | 6.8 |
| Eclipse | 7.4 | 8.1 |
| Estate | 5.9 | 7.9 |
| Fairfax | 4.9 | 6.6 |
| Georgetown | 6.3 | 8.0 |
| Glade | 4.8 | 4.8 |
| Gnome | 5.7 | 7.6 |
| Haga | 5.9 | 7.2 |
| Kelly | 5.1 | 7.2 |
| Kenblue | 1.8 | 1.2 |
| Liberty | 6.8 | 8.1 |
| Merion | 7.3 | 8.0 |
| Merit | 5.4 | 7.4 |
| Midnight | 6.6 | 8.1 |
| Monopoly | 5.2 | 7.1 |
| Nassau | 6.2 | 8.2 |
| Ram 1 | 4.9 | 3.4 |
| So. Dakota | 1.8 | 2.2 |
| Touchdown | 6.3 | 7.4 |
| Viva | 5.1 | 7.4 |
| LSD (.05) | 0.7 | 0.9 |

Leaf Spot Rating Scale: 1–9; 9 = No Disease
*Locations: Post, Falls, ID; North Brunswick, NJ; Adelphia, NJ; Marysville, OH
**Locations: Post Falls, ID; North Brunswick, NJ; Adelphia, NJ.

TABLE 20

A Comparison of Dollar Spot Disease Incidence in Ba 78-258 and Other Kentucky Bluegrass Varieties in Three (3) Tests Conducted at Various Locations in the U.S.

| | Means | | |
|---|---|---|---|
| Variety | Test 1* | Test 2** | Test 3*** |
| Ba 78-258 | 7.0 | 6.2 | 8.3 |
| Ba 77-700 | 7.0 | 7.0 | 7.7 |
| Abbey | 6.8 | 6.3 | 8.3 |
| Able 1 | 6.8 | 6.1 | 7.7 |
| Allure | 6.4 | 5.3 | 6.0 |
| Ascot | 7.8 | 7.0 | 8.3 |
| A-34 | 6.7 | 6.0 | 8.7 |
| Banff | 6.4 | 6.2 | 8.7 |
| Baron | 6.9 | 6.8 | 8.0 |
| Buckingham | 7.9 | 4.8 | 8.3 |
| Cannon | 6.6 | 6.4 | 8.7 |
| Challenger | 6.4 | 4.7 | — |
| Classic | 7.4 | 6.3 | 8.5 |
| Coventry | 5.9 | 5.9 | 7.0 |
| Eclipse | 7.5 | 7.2 | 8.3 |
| Estate | 5.3 | 5.6 | 8.0 |
| Fairfax | 5.8 | 6.0 | 6.5 |
| Georgetown | 6.9 | 6.1 | 8.3 |
| Glade | 7.0 | 6.4 | 7.7 |
| Gnome | 6.7 | 6.1 | 8.3 |
| Haga | 6.3 | 6.2 | 8.3 |
| Kelly | 7.3 | 6.3 | 8.3 |
| Kenblue | 6.8 | 6.8 | 8.7 |
| Liberty | 7.3 | 6.8 | 8.0 |
| Merion | 6.9 | 6.1 | 8.0 |
| Merit | 6.8 | 6.7 | 8.0 |
| Midnight | 8.0 | 6.6 | 8.3 |
| Monopoly | 7.1 | 6.7 | 7.7 |
| Nassau | 7.4 | 6.7 | 8.3 |
| Ram 1 | 6.0 | 4.9 | 6.3 |
| So. Dakota | 7.3 | 5.8 | 8.5 |

TABLE 20-continued

A Comparison of Dollar Spot Disease Incidence in Ba 78-258 and Other Kentucky Bluegrass Varieties in Three (3) Tests Conducted at Various Locations in the U.S.

| | Means | | |
|---|---|---|---|
| Variety | Test 1* | Test 2** | Test 3*** |
| Touchdown | 6.8 | 6.1 | 7.3 |
| Viva | 7.1 | 6.2 | 8.0 |
| LSD (.05) | 1.1 | 0.8 | 1.1 |

Dollar Spot Rating Scale: 1–9; 9 = No Disease
*Locations: Urbana, IL; Adelphia, NJ; Kingston, RI; Haymarket, VA.
**Locations: Urbana, IL; Silver Spring, MD; Kingston, RI.
***Locations: Silver Spring, MD.

TABLE 21

A comparison of Stem Rust Disease Incidence in Ba 78-258 and Other Kentucky Bluegrass Varieties at Adelphia, NJ.

| Variety | Stem Rust |
|---|---|
| Ba 78-258 | 7.0 |
| Ba77-700 | 7.3 |
| Abbey | 7.0 |
| Able 1 | 3.3 |
| Allure | 6.3 |
| Ascot | 7.3 |
| A-34 | 4.3 |
| Banff | 7.7 |
| Baron | 7.0 |
| Buckingham | 5.7 |
| Cannon | 7.3 |
| Challenger | 4.0 |
| Classic | 8.0 |
| Coventry | 6.7 |
| Eclipse | 4.0 |
| Estate | 6.3 |
| Fairfax | 6.3 |
| Georgetown | 8.7 |
| Glade | 7.7 |
| Gnome | 7.0 |
| Haga | 8.0 |
| Kelly | 8.0 |
| Kenblue | 5.7 |
| Liberty | 7.7 |
| Merion | 1.0 |
| Merit | 6.3 |
| Midnight | 8.0 |
| Monopoly | 6.3 |
| Nassau | 8.0 |
| Ram 1 | 8.0 |
| So. Dakota | 4.3 |
| Touchdown | 2.3 |
| Viva | 6.7 |
| LSD (.05) | 1.4 |

Stem Rust Rating Scale: 1–9; 9 = No Disease

TABLE 22

A Comparison of Leaf Rust Disease Incidence in Ba 78-258 and Other Kentucky Bluegrass Varieties at Kingston, RI.

| Variety | Leaf Rust |
|---|---|
| Ba 78-258 | 7.3 |
| Ba77-700 | 8.0 |
| Abbey | 6.3 |
| Able 1 | 7.0 |
| Allure | 6.0 |
| Ascot | 6.0 |
| A-34 | 6.0 |
| Banff | 7.0 |

TABLE 22-continued

A Comparison of Leaf Rust Disease Incidence in Ba 78-258 and Other Kentucky Bluegrass Varieties at Kingston, RI.

| Variety | Leaf Rust |
|---|---|
| Baron | 8.3 |
| Buckingham | 6.7 |
| Cannon | 6.3 |
| Challenger | 5.7 |
| Classic | 8.7 |
| Coventry | 7.0 |
| Eclipse | 5.7 |
| Estate | 6.3 |
| Fairfax | 6.0 |
| Georgetown | 7.7 |
| Glade | 7.0 |
| Gnome | 6.7 |
| Haga | 7.0 |
| Kelly | 5.0 |
| Kenblue | 6.7 |
| Liberty | 7.3 |
| Merion | 2.3 |
| Merit | 6.0 |
| Midnight | 6.0 |
| Monopoly | 5.3 |
| Nassau | 7.0 |
| Ram 1 | 6.7 |
| So. Dakota | 6.7 |
| Touchdown | 3.7 |
| Viva | 5.7 |
| LSD (.05) | 2.4 |

Leaf Rust Range Scale: 1–9; 9 = No Disease

TABLE 23

A Comparison of Brown Patch Disease Incidence in Ba 78-258 and Other Kentucky Bluegrass Varieties at Haymarket, VA.

| Variety | Brown Patch |
|---|---|
| Ba 78-258 | 8.7 |
| Ba77-700 | 6.0 |
| Abbey | 9.0 |
| Able 1 | 8.3 |
| Allure | 7.7 |
| Ascot | 8.7 |
| A-34 | 7.3 |
| Banff | 8.0 |
| Baron | 7.7 |
| Buckingham | 7.0 |
| Cannon | 8.7 |
| Challenger | 6.0 |
| Classic | 7.0 |
| Coventry | 6.7 |
| Eclipse | 7.3 |
| Estate | 7.0 |
| Fairfax | 5.3 |
| Georgetown | 6.7 |
| Glade | 8.3 |
| Gnome | 7.7 |
| Haga | 7.0 |
| Kelly | 7.0 |
| Kenblue | 5.3 |
| Liberty | 7.0 |
| Merion | 7.0 |
| Merit | 8.7 |
| Midnight | 8.3 |
| Monopoly | 7.0 |
| Nassau | 8.0 |
| Ram 1 | 6.7 |
| So. Dakota | 6.3 |
| Touchdown | 8.3 |

TABLE 23-continued

A Comparison of Brown Patch Disease Incidence in Ba 78-258 and Other Kentucky Bluegrass Varieties at Haymarket, VA.

| Variety | Brown Patch |
|---|---|
| Viva | 7.7 |
| LSD (.05) | 2.4 |

Brown Patch Rating Scale: 1–9; 9 = No Disease

TABLE 24

A Comparison of Stripe Rust Disease Incidence in Ba 78-258 and Other Kentucky Bluegrass Varieties at Gervais, OR.

| Variety | Stripe Rust |
|---|---|
| Ba 78-258 | 3.6 |
| Ba77-700 | 3.6 |
| Ba 78-165 | 6.0 |
| Abbey | 4.0 |
| Allure | 2.4 |
| Ascot | 6.4 |
| Bristol | 4.6 |
| Buckingham | 4.6 |
| Cannon | 5.6 |
| Chateau | 2.4 |
| Coventry | 1.8 |
| Estate | 2.8 |
| Fairfax | 2.6 |
| Gnome | 4.2 |
| Kelly | 5.8 |
| Newport | 8.8 |
| Victa | 6.4 |
| Viva | 4.4 |
| LSD (.05) | 1.6 |

Stripe Rust Rating Scale: 1–9; 9 = Most Rust

Additional comparisons for sod strength, *Poa annua* content, mature plant height, vegetative growth versus seed heads, panicle length, days to heading, days to anthesis and seed yields are presented in Tables 25–32.

TABLE 25

A Comparison of Sod Strength of Ba 78-258 and Other Kentucky Bluegrass Varieties at Haymarket, VA.

| Variety | Sod Strength |
|---|---|
| Ba 78-258 | 36.0 |
| Ba77-700 | 34.3 |
| Abbey | 49.7 |
| Able 1 | 31.3 |
| Allure | 34.3 |
| Ascot | 27.7 |
| A-34 | 29.0 |
| Banff | 33.3 |
| Baron | 38.3 |
| Buckingham | 26.0 |
| Cannon | 29.0 |
| Challenger | 31.7 |
| Classic | 28.3 |
| Coventry | 36.3 |
| Eclipse | 26.3 |
| Estate | 35.3 |
| Fairfax | 32.0 |
| Georgetown | 24.3 |
| Glade | 21.0 |
| Gnome | 39.0 |
| Haga | 26.7 |
| Kelly | 39.7 |
| Kenblue | 31.7 |
| Liberty | 27.7 |

TABLE 25-continued

A Comparison of Sod Strength of Ba 78-258 and Other Kentucky Bluegrass Varieties at Haymarket, VA.

| Variety | Sod Strength |
|---|---|
| Merion | 27.7 |
| Merit | 41.0 |
| Midnight | 26.7 |
| Monopoly | 28.7 |
| Nassau | 21.7 |
| Ram 1 | 36.3 |
| So. Dakota | 18.3 |
| Touchdown | 38.7 |
| Viva | 31.0 |
| LSD (.05) | 12.7 |

Sod Strength Measured in Kilograms of Tension

TABLE 26

A Comparison of *Poa Annua* Content of Ba 78-258 and Other Kentucky Bluegrass Varieties Based on Pooled Data from Halsey, Hubbard and Gervais, OR.

| Variety | *Poa Annua* Content |
|---|---|
| Ba 78-258 | 7.7 |
| Ba77-700 | 6.3 |
| Abbey | 5.7 |
| Able 1 | 5.0 |
| Allure | 7.3 |
| Ascot | 4.0 |
| A-34 | 5.7 |
| Banff | 8.7 |
| Baron | 7.3 |
| Buckingham | 6.7 |
| Cannon | 6.7 |
| Challenger | 7.7 |
| Classic | 8.3 |
| Coventry | 5 0 |
| Eclipse | 5.0 |
| Estate | 6.3 |
| Fairfax | 7.3 |
| Georgetown | 8.3 |
| Glade | 6.7 |
| Gnome | 4.7 |
| Haga | 8.7 |
| Kelly | 4.7 |
| Kenblue | 8.0 |
| Liberty | 7.7 |
| Merion | 1.7 |
| Merit | 6.3 |
| Midnight | 6.3 |
| Monopoly | 8.0 |
| Nassau | 7.7 |
| Ram 1 | 8.3 |
| So. Dakota | 7.3 |
| Touchdown | 7.3 |
| Viva | 6.0 |
| LSD (.05) | 1.8 |

*Poa annua* Content Rating Scale: 1–9; 9 = No Poa annua

TABLE 27

A Comparison of Mature Plant Height of Ba 78-258 and Other Kentucky Varieties at Gervais, OR.

| Variety | Height (cm) |
|---|---|
| Ba 78-258 | 60.3 |
| Ba77-700 | 60.0 |
| Ba 78-165 | 53.4 |
| Abbey | 65.0 |
| Allure | 53.0 |
| Ascot | 56.0 |

TABLE 27-continued

A Comparison of Mature Plant Height of Ba 78-258 and Other Kentucky Varieties at Gervais, OR.

| Variety | Height (cm) |
|---|---|
| Bristol | 69.4 |
| Buckingham | 66.8 |
| Cannon | 68.4 |
| Chateau | 60.2 |
| Coventry | 62.4 |
| Estate | 57.4 |
| Fairfax | 60.6 |
| Gnome | 60.8 |
| Kelly | 65.2 |
| Newport | 74.9 |
| Victa | 68.2 |
| Viva | 61.6 |
| LSD (.05) | 8.7 |

TABLE 28

A Comparison of Vegetative Growth Versus Seed Heads of Ba 78-258 and Other Kentucky Bluegrass Varieties at Gervais, OR.

| Variety | Vegetative Growth vs. Seed Heads |
|---|---|
| Ba 78-258 | 6.9 |
| Ba77-700 | 7.2 |
| Ba 78-165 | 5.8 |
| Abby | 5.8 |
| Allure | 7.2 |
| Ascot | 4.2 |
| Bristol | 6.0 |
| Buckingham | 5.6 |
| Cannon | 8.0 |
| Chateau | 6.8 |
| Coventry | 8.0 |
| Estate | 8.6 |
| Fairfax | 7.2 |
| Gnome | 6.6 |
| Kelly | 4.8 |
| Newport | 3.4 |
| Victa | 7.8 |
| Viva | 7.2 |
| LSD (.05) | 1.8 |

Vegetative Growth versus Seed Heads Rating Scale: 1–9; 9 = Most vegetative Growth

TABLE 29

A Comparison of Panicle Length of Ba 78-258 and Kentucky Bluegrass Varieties at Gervais, OR.

| Variety | Panicle Length (cm) |
|---|---|
| Ba 78-258 | 11.1 |
| Ba77-700 | 8.9 |
| Ba 78-165 | 8.6 |
| Abby | 10.4 |
| Allure | 7.8 |
| Ascot | 9.5 |
| Bristol | 13.6 |
| Buckingham | 11.9 |
| Cannon | 9.9 |
| Chateau | 7.7 |
| Coventry | 7.8 |
| Estate | 8.3 |
| Fairfax | 9.1 |
| Gnome | 9.7 |
| Kelly | 9.7 |
| Newport | 10.8 |

TABLE 29-continued

A Comparison of Panicle Length of Ba 78-258 and Kentucky Bluegrass Varieties at Gervais, OR.

| Variety | Panicle Length (cm) |
|---|---|
| Victa | 10.0 |
| Viva | 9.8 |
| LSD (.05) | 2.0 |

TABLE 30

A Comparison of Days to Heading of Ba 78-258 and Other Kentucky Bluegrass Varieties at Gervais, OR

| | Days to Heading | | |
|---|---|---|---|
| Variety | First | 50% | 100% |
| Ba 78-258 | 110.1 | 125.5 | 128.1 |
| Ba77-700 | 109.8 | 125.4 | 127.2 |
| Ba 78-165 | 100.2 | 118.6 | 121.6 |
| Abby | 108.2 | 124.2 | 127.2 |
| Allure | 110.6 | 125.0 | 126.2 |
| Ascot | 88.0 | 112.0 | 118.6 |
| Bristol | 95.4 | 118.6 | 122.2 |
| Buckingham | 94.0 | 112.4 | 120.0 |
| Cannon | 113.4 | 125.0 | 127.0 |
| Chateau | 106.0 | 123.8 | 126.0 |
| Coventry | 105.8 | 122.4 | 124.6 |
| Estate | 105.8 | 123.8 | 125.6 |
| Fairfax | 102.6 | 121.6 | 124.4 |
| Gnome | 109.8 | 125.4 | 127.2 |
| Kelly | 112.2 | 125.4 | 127.2 |
| Newport | 85.0 | 109.8 | 118.2 |
| Victa | 111.6 | 125.0 | 127.0 |
| Viva | 109.4 | 125.0 | 127.2 |
| LSD 0.05 | 5.3 | 4.0 | 1.8 |

TABLE 31

A Comparison of Days to Anthesis of Ba 78-258 and Other Kentucky Bluegrass Varieties at Gervais, OR

| | Days to Anthesis | | |
|---|---|---|---|
| Variety | First | 50% | 100% |
| Ba 78-258 | 129.1 | 134.1 | 137.5 |
| Ba77-700 | 129.0 | 134.4 | 137.8 |
| Ba 78-165 | 124.2 | 126.2 | 132.0 |
| Abbey | 129.2 | 132.4 | 136.6 |

TABLE 31-continued

A Comparison of Days to Anthesis of Ba 78-258 and Other Kentucky Bluegrass Varieties at Gervais, OR

| | Days to Anthesis | | |
|---|---|---|---|
| Variety | First | 50% | 100% |
| Allure | 127.8 | 131.0 | 134.8 |
| Ascot | 118.6 | 123.8 | 131.8 |
| Bristol | 124.6 | 126.6 | 132.0 |
| Buckingham | 123.4 | 127.6 | 133.6 |
| Cannon | 129.0 | 132.2 | 136.0 |
| Chateau | 128.2 | 130.8 | 135.2 |
| Coventry | 126.6 | 128.6 | 134.4 |
| Estate | 127.0 | 129.2 | 135.2 |
| Fairfax | 125.8 | 128.8 | 132.8 |
| Gnome | 129.0 | 133.2 | 136.6 |
| Kelly | 129.0 | 132.8 | 136.6 |
| Newport | 120.4 | 123.4 | 131.4 |
| Victa | 129.0 | 132.2 | 136.0 |
| Viva | 129.0 | 132.8 | 136.6 |
| LSD (0.05) | 2.1 | 2.5 | 1.8 |

TABLE 32

A Comparison of Seed Yields of Ba 78-258 and Other Kentucky Bluegrass Varieties in Three (3) Tests Conducted at Imbler, OR.

| | Seed Yield (Lbs./acre) | | |
|---|---|---|---|
| Variety | Test 1 | Test 2 | Test 3 |
| Ba 78-258 | 1,377 | 1,211 | 1,076 |
| Ba77-700 | 1,569 | 1,105 | 1,156 |
| Abbey | 1,549 | 1,324 | 1,090 |
| Buckingham | 748 | 923 | 740 |
| Cannon | 1,551 | 1,130 | 1,171 |
| Coventry | 1,046 | 839 | 847 |
| Fairfax | 1,159 | 1,074 | 766 |
| Viva | 1,612 | 1,111 | 1,054 |
| LSD (.05) | 160 | 271 | 296 |

What is claimed is:

1. A variety of Kentucky Bluegrass plant, substantially as shown and described, characterized by a medium to high level of resistance to a broad spectrum of serious diseases including leaf spot and melting out, dollar spot, rusts and brown patch; a dark green color throughout the growing season; a medium to high quality turf formation under a wide variety of environmental conditions; a moderately wide blade; a strong root system and a high level of seed yielding capacity.

* * * * *

UNITED STATES PATENT AND TRADEMARK OFFICE

CERTIFICATE OF CORRECTION

PATENT NO. : PP 10,384
DATED : May 5, 1998
INVENTOR(S) : Virgil D. Meier et al.

It is certified that error appears in the above-identified patent and that said Letters Patent is hereby corrected as shown below:

Column 2,
Line 13, change "goof" to -- good --.
Line 14, change "evidence" to -- evidenced --.
Lines 31, 32, 38 & 40, change "dosal" to -- dorsal --.
Line 35, change "gases" to -- grasses --.

Column 6,
Table 6, in the headings, change "Dosal" (2 occurrences) to -- Dorsal --.
Table 7, first line of the title, delete "Numbers".
Table 7, under the heading "Width mm", change "0.8" to -- 0.08 --.
Table 8, in the headings, change "Dosal" (2 occurrences) to -- Dorsal --.

Column 7,
Line 5, of the second paragraph, change "with" to -- and --.
Line 13, of the second paragraph, change "5 Gy" to -- 5 GY --.

Column 8,
Table 9, in the headings, change "Fort Collins" to -- Fort Collins CO --; change "Post Falls" to -- Post Falls ID --; change "Lexington" to -- Lexington KY --; change "Marysville" to -- Marysville, OH --; change "Beltsville" to -- Beltsville UB --; and change "Blacksburg" to -- Blacksburg VA --.

Signed and Sealed this

Fourteenth Day of October, 2003

JAMES E. ROGAN
*Director of the United States Patent and Trademark Office*